(12) United States Patent
Majeed

(10) Patent No.: US 8,329,743 B2
(45) Date of Patent: Dec. 11, 2012

(54) COMPOSITIONS AND ITS USE IN TREATING OBESITY OR INDUCING WEIGHT LOSS

(75) Inventor: Muhammed Majeed, East Windsor, NJ (US)

(73) Assignee: Sami Labs Limited, Bangalore (IN)

( * ) Notice: Subject to any disclaimer, the term of this patent is extended or adjusted under 35 U.S.C. 154(b) by 92 days.

(21) Appl. No.: 12/987,326

(22) Filed: Jan. 10, 2011

(65) Prior Publication Data

US 2012/0178801 A1 Jul. 12, 2012

(51) Int. Cl.
*A61K 31/35* (2006.01)
*C12N 5/02* (2006.01)

(52) U.S. Cl. ........................................ 514/456; 435/375
(58) Field of Classification Search .................. 514/456; 435/375
See application file for complete search history.

(56) References Cited

U.S. PATENT DOCUMENTS 7,063,861 B2 * 6/2006 Majeed et al. ................. 424/451
2002/0187943 A1 * 12/2002 Majeed et al. ................... 514/27

* cited by examiner

*Primary Examiner* — Raymond Henley, III

(57) ABSTRACT

The present invention provides a composition comprising polyisoprenylated benzophenone derivative and at least one component selected from stilbene derivative and anthocyanins. The composition inhibits adipogenesis and is therefore useful in treating obesity or weight loss.

14 Claims, 3 Drawing Sheets

COMPOSITIONS AND ITS USE IN TREATING OBESITY OR INDUCING WEIGHT LOSS

FIELD OF THE INVENTION

Figure 1:
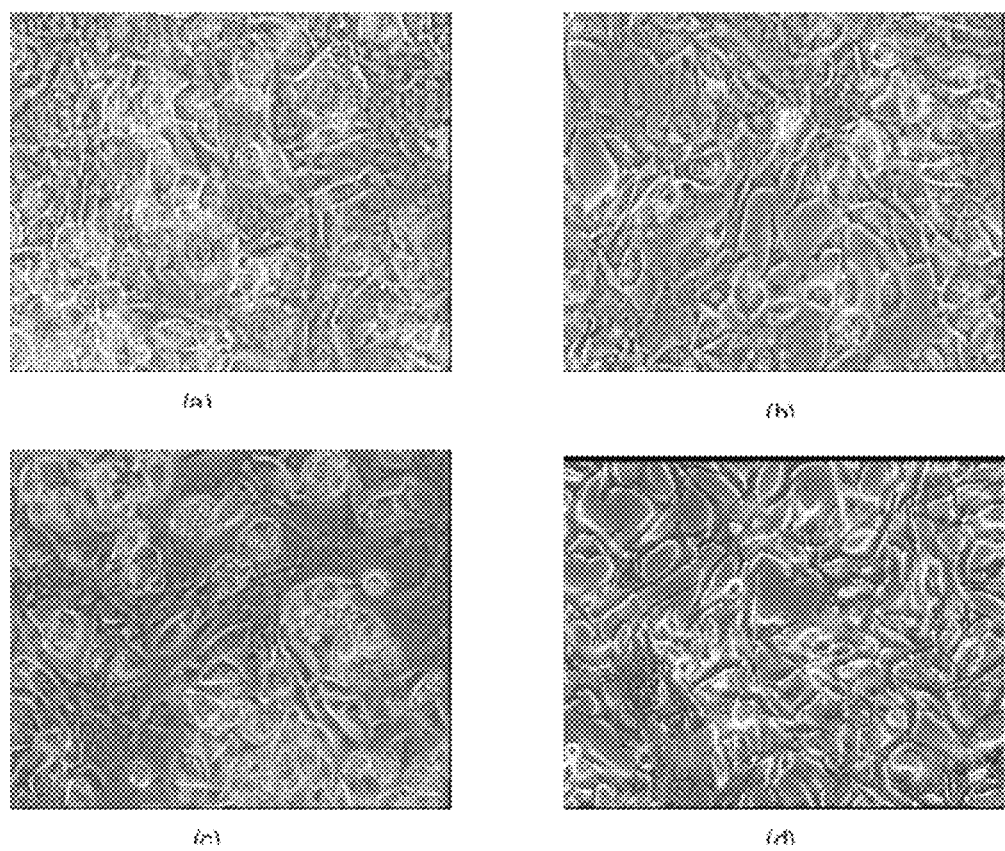

The present invention relates to a composition comprising polyisoprenylated benzophenone derivative and at least one component selected from stilbene derivative and anthocyanins. More specifically, the composition of the present invention comprise garcinol/guttiferones and at least one of pterostilbene and anthocyanins. The composition inhibits adipogenesis and therefore is useful in treating obesity or weight loss.

BACKGROUND OF PRIOR ART

Adipogenesis is the formation of fat or fatty tissue. A fat cell develops as internally produced lipid droplets coalesce into a single large mass. More recently, studies of adipogenesis have proceeded with the hope that manipulation of this process in humans might lead to a reduction in the burden of obesity and diabetes.

Obesity, defined as an increase in adipose tissue mass, is the most prevalent nutritional disorder in industrialized countries and is a growing problem in developing countries. An increase in adipose tissue mass can be the result of the production of new fat cells through the process of adipogenesis and/or the deposition of increased amounts of cytoplasmic triglyceride per cell. Eventually, cellulite results due to enhanced adipogenesis and accumulation of chunks of adipocytes under the skin dermis.

Obesity is described as a global epidemic and overweight and obese individuals (BMI of 25 and above) are at increased risk for various chronic physical ailments and psychological problems such as depression, eating disorders and low self esteem.

The prevalence of overweight and obesity is increasing throughout the world's population. The World Health Organization (WHO) reports that more than one billion adults are overweight and at least 300 million of them are clinically obese. WHO considers obesity to be one of the top 10 causes of preventable death worldwide.

There is a constant need and search for safe natural approach to help manage obesity and its related socio-economic consequences.

Garcinol, a polyisoprenylated benzophenone derivative isolated from Garcinia species is a well-known anti-oxidant (i.e., emulsified garcinol suppressed superoxide anion comparably to DL alpha-tocopherol), anti-carcinogen and also has anti-microbial properties.

Garcinol, isolated from Garcinia sp. fruit rind exhibits anti-oxidant and chemoprotective properties (1). In one experiment, rats fed a garcinol diet (0.01% and 0.05%) showed a significantly reduced development of azoxymethane (AOM)-induced colonic aberrant crypt foci (ACF) as compared to control animals. Feeding of garcinol significantly elevated liver glutathione S-transferase, quinone reductase activities, suppressed $O_2$ and NO generation and expression of iNOS and COX-2 proteins. These findings suggest a possible chemopreventive mechanism of garcinol.

Garcinol and isogarcinol were evaluated for their antibacterial activity against methicillin-resistant *Staphylococcus aureus* (2). These compounds showed a minimum inhibitory concentration at 3.1-12.5 micrograms/ml, or nearly equal to that of the antibiotic, vancomycine.

Garcinol's role as a potent inhibitor of histone acetyltransferases (HATs) both in vitro and in vivo was reported by Tapas et al in 2004 ("Polyisoprenylated Benzophenone, Garcinol, a Natural Histone Acetyltransferase Inhibitor, Represses Chromatin Transcription and Alters Global Gene Expression", The Journal of Biological Chemistry, Vol. 279, No. 32, Issue of August 6, pp. 33716-33726, 2004)

Anthocyanins are one class of flavanoid compounds, which are widely distributed plant polyphenols. They occur in all tissues of higher plants, including leaves, stems, roots, flowers, and fruits. There is considerable evidence that dietary anthocyanin pigments have preventative and therapeutic roles in a number of human diseases. The chemical basis for these desirable properties of anthocyanins is believed to be related to their antioxidant capacity, ability to scavenge and trap free radicals that damage biomolecules.

In 1982, N. Krishnamurthy et al. (3) isolated anthocyanin pigments from the fresh red ripe fruits of Kokam (*Garcinia indica*). The rind portion was separated from the rest of the fruit and was macerated in a blender using methanol containing 1% HCl for three times. The extracts were combined, filtered and concentrated in vacuo at 30° C. Paper chromatography of the Kokam pigment extract showed two anthocyanin bands. The slower moving band was designated as B1 and the other B2. The total anthocyanin concentration was estimated to be 2.4 percent on a dry weight basis; the ratio of B1 to B2 is 1:4.

Majeed et al (U.S. Pat. No. 7,063,861) discloses a composition comprising hydroxycitric acid in combination with either one or both of garcinol and anthocyanin and its use in weight loss therapy in animal subjects.

It is reported that dietary resveratrol (3,4',5-trihydroxy-trans-stilbene) at 50 parts per million suppressed blood serum lipid peroxidase levels in rats and dose-dependently suppressed serum triglyceride levels, VLDL and LDL cholesterol levels [Miura, D.; Miura, Y.; Yagasaki, K. Hypolipidemic action of dietary resveratrol, a phytoalexin in grapes and red wine, in hepatoma-bearing rats. Life Sci. 2003, 73, 1393-400]. Naokatu Arakaki et al reported that treatment of differentiated 3T3-L1 adipocytes with $H^+$-ATP synthase inhibitors (resveratrol; piceatannol) lead to a decrease in cytosolic lipid droplet accumulation.

Rimando et al document that pterostilbene (3,5-dimethoxy-4'-hydroxystilbene), a natural analog of resveratrol acts as a PPARα agonist and may be a more effective hypo-lipidemic agent than resveratrol itself [J. Agric. Food Chem. 2005, 53, 3403-3407]. This documentation is further validated by Marudhamuthu Amarnath Sateesh and Leelavinothan Pari, who observed that pterostilbene significantly, lowered levels of triglycerides, phospholipids, free fatty acids and total cholesterol in the serum, liver and kidneys of diabetic rats [Journal of Applied Biomedicine, Volume 5 (2008), No 1).

The present invention provides a composition for inhibiting adipogenesis and thereby its use in treating obesity or weight loss.

BRIEF DESCRIPTION OF ACCOMPANYING FIGURES

FIG. 1: shows the effect of treatment of adipocyte cells with (b) garcinol (c) pterostilbene and (d) anthocyanins. FIG. 1 (*a*) represents untreated adipocytes.

Figure 2:
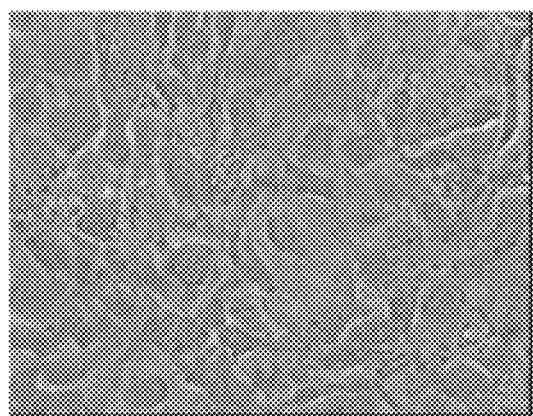
Figure 2:
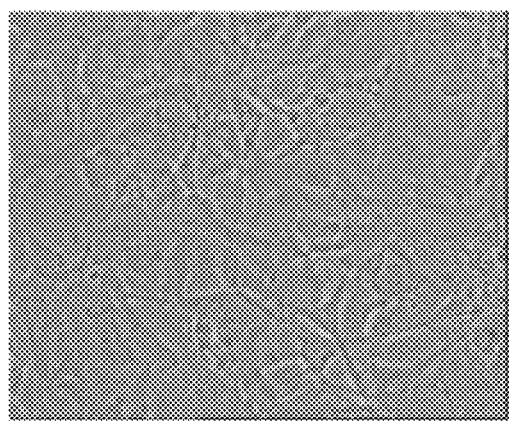

FIG. 2: shows the effect of treatment of adipocyte cells with (a) garcinol+pterostilbene and (b) garcinol+pterostilbene+anthocyanins.

Figure 3:
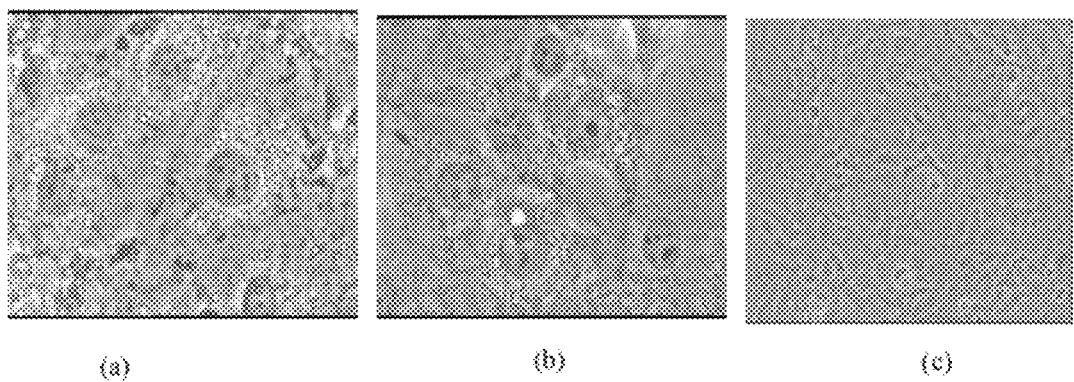

FIG. 3: shows inhibition of Adipogenesis in 3T3 µl mouse adipocytes (Oil Red O staining) by (b) garcinol+pterostilbene and (c) garcinol+pterostilbene+anthocyanins. FIG. 3 (a) represents untreated adipocytes.

DETAILED DESCRIPTION OF INVENTION

The present invention relates to a composition comprising polyisoprenylated benzophenone derivative and at least one component selected from stilbene derivative and anthocyanins optionally along with pharmaceutically acceptable excipients.

In another embodiment of the present invention, the ratio of polyisoprenylated benzophenone derivative and stilbene derivative is 1:1.

In yet another embodiment of the present invention, the ratio of polyisoprenylated benzophenone derivative, stilbene derivative and anthocyanins is 1:1:1.

In still another embodiment of the present invention, wherein the polyisoprenylated benzophenone derivative is selected from a group comprising garcinol, isogarcinol, xanthochymol, isoxanthochymol and guttiferones.

In still another embodiment of the present invention, the stilbene derivative is selected from a group comprising resveratrol, piceatannol, oxyresveratrol, pterostilbene and 3-hydroxypterostilbene.

In still another embodiment of the present invention, the composition comprises garcinol/guttiferones and at least one of pterostilbene and anthocyanins optionally along with pharmaceutically acceptable excipients.

In still another embodiment of the present invention, the pharmaceutically acceptable excipients are selected from a group comprising antiadherents, binding agents, coating agents, disintegrating agents, fillers and diluents, flavoring agents, colorants, glidants, lubricants, preservatives, sorbents, sweeteners and combinations thereof.

In still another embodiment of the present invention, the composition is formulated into dosage forms selected from a group comprising liquid, troches, lozenges, powder, granule, capsule, tablet, patch, gel, emulsion, cream, lotion, dentrifice, drop, suspension, syrups, elixirs, phyotceuticals and neutraceuticals.

The present invention relates to a process for preparing a composition comprising polyisoprenylated benzophenone derivative and at least one component selected from stilbene derivative and anthocyanins optionally along with pharmaceutically acceptable excipients, said process comprising step of combining polyisoprenylated benzophenone derivative with stilbene derivative or anthocyanins or with both optionally along with pharmaceutically acceptable excipients to obtain the composition.

In still another embodiment of the present invention, the ratio of polyisoprenylated benzophenone derivative and stilbene is 1:1.

In still another embodiment of the present invention, the ratio of polyisoprenylated benzophenone derivative, stilbene derivative and anthocyanins is 1:1:1.

In still another embodiment of the present invention, the polyisoprenylated benzophenone derivative is selected from a group comprising garcinol, isogarcinol, xanthochymol, isoxanthochymol and guttiferones and the stilbene derivative is selected from a group comprising resveratrol, piceatannol, oxyresveratrol, pterostilbene and 3-hydroxypterostilbene.

The present invention relates to a method of decreasing lipid accumulation in a fat cell, said method comprising contacting the fat cell with an effective amount of a composition comprising polyisoprenylated benzophenone derivative and at least one component selected from stilbene derivative and anthocyanins optionally along with pharmaceutically acceptable excipients.

In still another embodiment of the present invention, the polyisoprenylated benzophenone derivative is selected from a group comprising garcinol, isogarcinol, xanthochymol, isoxanthochymol and guttiferones and the stilbene derivative is selected from a group comprising resveratrol, piceatannol, oxyresveratrol, pterostilbene and 3-hydroxypterostilbene.

The present invention relates to a method of inhibiting adipogenesis or treating obesity, said method comprising administering to a subject in need thereof an effective amount of composition comprising polyisoprenylated benzophenone derivative and at least one component selected from stilbene derivative and anthocyanins optionally along with pharmaceutically acceptable excipients.

In still another embodiment of the present invention, the subject is animal including human beings.

In still another embodiment of the present invention, wherein the polyisoprenylated benzophenone derivative is selected from a group comprising garcinol, isogarcinol, xanthochymol, isoxanthochymol and guttiferones and the stilbene derivative is selected from a group comprising resveratrol, piceatannol, oxyresveratrol, pterostilbene and 3-hydroxypterostilbene.

The present invention relates to a composition comprising polyisoprenylated benzophenone derivative and at least one component selected from stilbene derivative and anthocyanins.

The polyisoprenylated benzophenone derivative is selected from a group comprising garcinol, isogarcinol, xanthochymol, isoxanthochymol and guttiferones. Garcinol is a prominent member of structurally diverse polyprenylated benzophenone derivatives present in *Garcinia* species. There are structurally similar compounds that occur along with Garcinol such as Isogarcinol (formed through the cyclization of Garcinol), Xanthochymol, its cyclized analog, isoxanthochymol. Guttiferones have an additional isoprenyl unit added onto Garcinol molecular structure. In the composition of present invention, individual guttiferone compounds or the fraction containing guttiferones from *Garcinia* species is used.

Stilbene derivative is selected from a group comprising resveratrol, piceatannol, oxyresveratrol, pterostilbene and 3-hydroxypterostilbene. The source of 3-hydroxypterostilbene is *Sphaerophysa salsula* or it may be synthesized using pterostilbene.

More specifically, the composition comprises garcinol/guttiferones and at least one of pterostilbene and anthocyanins. The composition inhibits adipogenesis and therefore is useful in treating obesity or weight loss.

The composition containing garcinol/guttiferones and pterostilbene effectively inhibits adipogenesis when compared to the activity of components individually. Use of anthocyanins along with garcinol/guttiferones and pterostilbene enhances the adipogenesis inhibitory potential greater than that of the composition containing garcinol/guttiferones and pterostilbene. Thus, the composition of the present invention contains garcinol/guttiferones and at least one of pterostilbene and anthocyanins.

Garcinol/guttiferones and anthocyanins used in the present invention are extracted from *Garcinia* species, while pterostilbene from *Pterocarpus* species. The compounds are extracted from respective plant species by methods known in the art.

Garcinol/guttiferones, pterostilbene and anthocyanins may also be extracted from other sources or may be synthesized for use in the composition of present invention. All three components are used in the ratio of 1:1:1 in the composition. In a composition containing garcinol/guttiferones and pterostilbene, the ratio of the components is 1:1.

In a specific embodiment, the composition of the present invention contains garcinol/guttiferones with at least one of pterostilbene and anthocyanins. It is also understood that a person skilled in the art may arrive at the composition using derivatives of the compounds in various combinations.

The invention also relates to a process of obtaining the composition and its use in inhibiting adipogenesis and thereby treatment of obesity.

The invention is elaborated with the help of following examples. However, these should not be construed to limit the scope of invention.

EXAMPLE 1

Adipogenesis, or the development of fat cells from preadipocytes, has been one of the most intensely studied models for obesity. A fat cell develops as internally produced lipid droplets coalesce into a single large mass. The in vitro adipogenesis inhibitory model can recapitulate most of the critical aspects of fat cell formation in vivo.

A common assay to measure adipocyte differentiation in cell culture is with the dye Oil Red-O, which is a lipid-soluble red dye. Since terminal differentiation of adipocytes is accompanied by the accumulation of great amounts of lipids in large cytoplasmic vesicles, a strong, bright, staining of the cytoplasm with this dye is a reliable indicator of adipocyte differentiation.

Methodology:

3T3-L1 mouse adipocyte cells are seeded at a density of 5000 cell/200 µl of adipocyte induction medium in a 96 well plate. After 48 hrs, sample is added. After 72 hrs, the medium is changed to adipocyte progression medium along with the sample. The medium is similarly changed after another 48 hours. The plates are washed gently after 48 hrs with 100 µl of PBS. 100 µl of 10% formalin is used to fix the cells for 30 min keeping at RT. The cells are then washed twice with 60% isopropanol gently. 100 µl of clear Oil red O stain is added to the wells & kept for staining for 1 hr. The cells are then washed with 70% Ethanol twice, once with PBS and air dried. Then 100 µl of 4% tritonx100 in isopropanol is added to all the wells, covered tightly & kept it in a shaker for 20 min at 25-30° C. The OD reading is taken at 492 nm in microplate reader.

The results are expressed as $IC_{50}$ values using Graphpad prism software. The percentage of inhibition of adipogenesis is calculated as follows, $$\% \text{ Inhibition} = \frac{C-T}{C} \times 100$$

Where C—absorbance due to adipogenesis in untreated cells
T—absorbance due to adipogenesis in sample treated cells The results from Table 1 clearly show that the adipogenesis inhibitory potential of the composition containing garcinol and pterostilbene is enhanced when compared to components individually. The composition containing garcinol, pterostilbene and anthocyanins shows greater inhibitory potential than the individual components and that of the composition containing garcinol and pterostilbene.

TABLE 1

Comparison of adipogenesis inhibitory activity of the composition of the present invention and the individual components

| Compound | Adipogenesis inhibitory activity (IC50) |
|---|---|
| Garcinol | 0.2 µg/ml |
| Pterostilbene | 13.32 µg/ml |
| Anthocyanins | 10.56 µg/ml |
| Garcinol + Pterostilbene (1:1) | 0.05 µg/ml |
| Garcinol + Pterostilbene + Anthocyanins (1:1:1) | 0.01 µg/ml |

It is also evident from the FIGS. 1, 2 and 3 that the accumulation of great amounts of lipids decreased in the adipocytes treated with the composition.

Table 2 shows that the adipogenesis inhibitory potential of the composition containing guttiferones and pterostilbene is enhanced when compared to components individually. The composition containing guttiferones, pterostilbene and anthocyanins shows greater inhibitory potential than the individual components and that of the composition containing guttiferones and pterostilbene.

TABLE 2

Comparison of adipogenesis inhibitory activity of the composition of the present invention and the individual components

| Compound | Adipogenesis inhibitory activity (IC50) |
|---|---|
| Guttiferones | 0.5 µg/ml |
| Pterostilbene | 13.32 µg/ml |
| Anthocyanins | 10.56 µg/ml |
| Guttiferones + Pterostilbene (1:1) | 0.1 µg/ml |
| Guttiferones + Pterostilbene + Anthocyanins (1:1:1) | 0.06 µg/ml |

REFERENCES

1. Tanaka, T. et. al, Prevention of colonic aberrant crypt foci by dietary feeding of garcinol in male F3444 rats. Carcinogenesis, June 2000: 21 (6): 1183-9.
2. Linuma M et al, Antibacterial activity of some *garcinia* benzophenone derivatives against methicillin-resistant *staphylococcus aureus*. Biol Pharm Bull 1996 February; 19(2): 311-4.
3. Krishnamurthy, N. et al. J Food Sci and Tech. 1982; 97.

The invention claimed is:

1. A composition comprising polyisoprenylated benzophenone and at least one component selected from stilbene and anthocyanins optionally along with pharmaceutically acceptable excipients.

2. The composition as claimed in claim 1, wherein the ratio of polyisoprenylated benzophenone and stilbene is 1:1.

3. The composition as claimed in claim 1, wherein the ratio of polyisoprenylated benzophenone, stilbene and anthocyanins is 1:1:1.

4. The composition as claimed in claim 1, wherein the polyisoprenylated benzophenone is selected from a group comprising garcinol, isogarcinol, xanthochymol, isoxanthochymol and guttiferones.

5. The composition as claimed in claim 1, wherein the stilbene is selected from a group comprising resveratrol, piceatannol, oxyresveratrol, pterostilbene and 3-hydroxypterostilbene.

6. The composition as claimed in claim 1, wherein the composition comprises garcinol/guttiferones and at least one of pterostilbene and anthocyanins optionally along with pharmaceutically acceptable excipients.

7. The composition as claimed in claim 1, wherein the pharmaceutically acceptable excipients are selected from a group comprising antiadherents, binding agents, coating agents, disintegrating agents, fillers and diluents, flavoring agents, colorants, glidants, lubricants, preservatives, sorbents, sweeteners and combinations thereof.

8. The composition as claimed in claim 1, wherein the composition is formulated into dosage forms selected from a group comprising liquid, troches, lozenges, powder, granule, capsule, tablet, patch, gel, emulsion, cream, lotion, dentrifice, drop, suspension, syrups, elixirs, phyotceuticals and neutraceuticals.

9. The composition as claimed in claim 1, wherein the composition is prepared by a process comprising step of combining polyisoprenylated benzophenone with stilbene or anthocyanins or with both optionally along with pharmaceutically acceptable excipients.

10. A method of decreasing lipid accumulation in a fat cell, said method comprising contacting the fat cell with an effective amount of a composition comprising polyisoprenylated benzophenone and at least one component selected from stilbene and anthocyanins optionally along with pharmaceutically acceptable excipients.

11. The method as claimed in claim 10, wherein the polyisoprenylated benzophenone is selected from a group comprising garcinol, isogarcinol, xanthochymol, isoxanthochymol and guttiferones and the stilbene is selected from a group comprising resveratrol, piceatannol, oxyresveratrol, pterostilbene and 3-hydroxypterostilbene.

12. A method of inhibiting adipogenesis or treating obesity, said method comprising administering to a subject in need thereof an effective amount of a composition comprising polyisoprenylated benzophenone and at least one component selected from stilbene and anthocyanins optionally along with pharmaceutically acceptable excipients.

13. The method as claimed in claim 12, wherein the subject is animal including human beings.

14. The method as claimed in claim 12, wherein the polyisoprenylated benzophenone is selected from a group comprising garcinol, isogarcinol, xanthochymol, isoxanthochymol and guttiferones and the stilbene is selected from a group comprising resveratrol, piceatannol, oxyresveratrol, pterostilbene and 3-hydroxypterostilbene.

* * * * *